(12) United States Patent
Armstrong et al.

(10) Patent No.: US 8,600,521 B2
(45) Date of Patent: Dec. 3, 2013

(54) IMPLANTABLE MEDICAL DEVICE HAVING MULTIPLE ELECTRODE/SENSOR CAPABILITY AND STIMULATION BASED ON SENSED INTRINSIC ACTIVITY

(75) Inventors: Randolph K. Armstrong, Houston, TX (US); Scott A. Armstrong, Danbury, TX (US)

(73) Assignee: Cyberonics, Inc., Houston, TX (US)

( * ) Notice: Subject to any disclaimer, the term of this patent is extended or adjusted under 35 U.S.C. 154(b) by 1944 days.

(21) Appl. No.: 11/045,602

(22) Filed: Jan. 27, 2005

(65) Prior Publication Data
US 2006/0167497 A1 Jul. 27, 2006

(51) Int. Cl.
*A61N 1/36* (2006.01)

(52) U.S. Cl.
USPC ............................ 607/117; 607/45; 607/118

(58) Field of Classification Search
USPC ............................................ 607/45, 117–118
See application file for complete search history.

(56) References Cited

U.S. PATENT DOCUMENTS

| | | | |
|---|---|---|---|
| 3,760,812 A | 9/1973 | Timm et al. | |
| 4,424,812 A * | 1/1984 | Lesnick | 607/30 |
| 4,459,989 A | 7/1984 | Borkan | |
| 4,573,481 A | 3/1986 | Bullara | |
| 4,590,946 A | 5/1986 | Loeb | |
| 4,608,985 A | 9/1986 | Crish et al. | |
| 4,612,934 A | 9/1986 | Borkan | |
| 4,628,942 A | 12/1986 | Sweeney et al. | |
| 4,649,936 A | 3/1987 | Ungar et al. | |
| 4,702,254 A | 10/1987 | Zabara | |
| 4,793,353 A | 12/1988 | Borkan | |
| 4,867,164 A | 9/1989 | Zabara | |
| 4,873,655 A | 10/1989 | Kondraske | |
| 4,920,979 A | 5/1990 | Bullara | |
| 5,003,975 A | 4/1991 | Hafelfinger et al. | |
| 5,025,807 A | 6/1991 | Zabara | |
| 5,095,905 A | 3/1992 | Klepinski | |
| 5,111,815 A | 5/1992 | Mower | |
| 5,205,285 A | 4/1993 | Baker, Jr. | |
| 5,304,206 A | 4/1994 | Baker, Jr. et al. | |

(Continued)

FOREIGN PATENT DOCUMENTS

| | | |
|---|---|---|
| WO | 2004036377 A2 | 4/2004 |
| WO | 2005028026 A1 | 3/2005 |

OTHER PUBLICATIONS

Bachman, D.S, et al., "Effects of Vagal Volleys and Serotonin on Units of Cingulate Cortex in Monkeys," Brain Research, 130, (1977), pp. 253-269.

(Continued)

*Primary Examiner* — Joseph Stoklosa
(74) *Attorney, Agent, or Firm* — Cyberonics, Inc.

(57) ABSTRACT

In one embodiment, an implantable neurostimulator comprises a pulse generator that generates an electrical pulse signal to stimulate a neural structure in a patient, a stimulation lead assembly coupled to the pulse generator for delivering the electrical pulse signal to the neural structure, a plurality of sensors coupled to the pulse generator, and sensor select logic. Each sensor is individually selectable and the sensor select logic selects any two or more of the plurality of sensors for sensing a voltage difference between the selected sensors. In other embodiments, two or more physiologic parameters are sensed. In yet another embodiment, a method comprises sensing intrinsic electrical activity on a person's nerve and stimulating the nerve based on the sensed intrinsic electrical activity of the nerve.

20 Claims, 10 Drawing Sheets

(56) References Cited

U.S. PATENT DOCUMENTS

| | | |
|---|---|---|
| 5,311,876 A | 5/1994 | Olsen et al. |
| 5,330,507 A | 7/1994 | Schwartz |
| 5,334,221 A | 8/1994 | Bardy |
| 5,356,425 A | 10/1994 | Bardy et al. |
| 5,411,528 A | 5/1995 | Miller et al. |
| 5,431,692 A | 7/1995 | Hansen et al. |
| 5,456,692 A | 10/1995 | Smith, Jr. et al. |
| 5,507,784 A | 4/1996 | Hill et al. |
| 5,507,786 A | 4/1996 | Morgan et al. |
| 5,540,734 A | 7/1996 | Zabara |
| 5,645,570 A | 7/1997 | Corbucci |
| 5,658,318 A | 8/1997 | Stroetmann et al. |
| 5,683,422 A | 11/1997 | Rise et al. |
| 5,690,681 A | 11/1997 | Geddes et al. |
| 5,700,282 A | 12/1997 | Zabara |
| 5,702,429 A | 12/1997 | King |
| 5,716,377 A | 2/1998 | Rise et al. |
| 5,792,186 A | 8/1998 | Rise |
| 5,814,092 A | 9/1998 | King |
| 5,833,709 A | 11/1998 | Rise et al. |
| 5,861,014 A | 1/1999 | Familoni |
| 5,913,882 A | 6/1999 | King |
| 5,916,239 A | 6/1999 | Geddes et al. |
| 5,928,272 A | 7/1999 | Adkins et al. |
| 5,978,702 A | 11/1999 | Ward et al. |
| 5,987,352 A | 11/1999 | Klein et al. |
| 5,995,868 A | 11/1999 | Osorio et al. |
| 6,018,682 A | 1/2000 | Rise |
| 6,061,593 A | 5/2000 | Fischell et al. |
| 6,083,249 A | 7/2000 | Familoni |
| 6,115,628 A | 9/2000 | Stadler et al. |
| 6,115,630 A | 9/2000 | Stadler et al. |
| 6,128,526 A | 10/2000 | Stadler et al. |
| 6,134,474 A | 10/2000 | Fischell et al. |
| 6,141,590 A | 10/2000 | Renirie et al. |
| 6,208,894 B1 | 3/2001 | Schulman et al. |
| 6,248,080 B1 | 6/2001 | Miesel et al. |
| 6,304,775 B1 | 10/2001 | Iasemidis et al. |
| 6,308,102 B1 | 10/2001 | Sieracki et al. |
| 6,324,421 B1 | 11/2001 | Stadler et al. |
| 6,327,503 B1 | 12/2001 | Familoni |
| 6,337,997 B1 | 1/2002 | Rise |
| 6,341,236 B1 | 1/2002 | Osorio et al. |
| 6,360,122 B1 | 3/2002 | Fischell et al. |
| 6,366,813 B1 | 4/2002 | DiLorenzo |
| 6,381,496 B1 | 4/2002 | Meadows et al. |
| 6,393,325 B1 | 5/2002 | Mann et al. |
| 6,397,100 B2 | 5/2002 | Stadler et al. |
| 6,418,348 B1 | 7/2002 | Witte |
| 6,459,936 B2 | 10/2002 | Fischell et al. |
| 6,473,639 B1 | 10/2002 | Fischell et al. |
| 6,473,653 B1 | 10/2002 | Schallhorn et al. |
| 6,477,417 B1 | 11/2002 | Levine |
| 6,477,418 B2 | 11/2002 | Plicchi et al. |
| 6,480,743 B1 | 11/2002 | Kirkpatrick et al. |
| 6,522,928 B2 | 2/2003 | Whitehurst et al. |
| 6,542,774 B2 | 4/2003 | Hill et al. |
| 6,549,804 B1 | 4/2003 | Osorio et al. |
| 6,587,727 B2 | 7/2003 | Osorio et al. |
| 6,594,524 B2 | 7/2003 | Esteller et al. |
| 6,597,954 B1 * | 7/2003 | Pless et al. ............... 607/62 |
| 6,600,956 B2 | 7/2003 | Maschino et al. |
| 6,628,987 B1 | 9/2003 | Hill et al. |
| 6,647,296 B2 | 11/2003 | Fischell et al. |
| 6,671,547 B2 | 12/2003 | Lyster et al. |
| 6,671,555 B2 | 12/2003 | Gielen et al. |
| 6,671,556 B2 | 12/2003 | Osorio et al. |
| 6,684,105 B2 | 1/2004 | Cohen et al. |
| 6,768,969 B1 | 7/2004 | Nikitin et al. |
| 6,801,805 B2 | 10/2004 | Stokes et al. |
| 6,819,953 B2 | 11/2004 | Yonce et al. |
| 6,832,114 B1 | 12/2004 | Whitehurst et al. |
| 6,853,862 B1 | 2/2005 | Marchal et al. |
| 6,885,888 B2 | 4/2005 | Rezai |
| 6,920,357 B2 | 7/2005 | Osorio et al. |
| 6,944,501 B1 | 9/2005 | Pless |
| 6,961,618 B2 | 11/2005 | Osorio et al. |
| 7,006,872 B2 | 2/2006 | Gielen et al. |
| 7,050,856 B2 | 5/2006 | Stypulkowski |
| 7,561,918 B2 * | 7/2009 | Armstrong et al. ............. 607/39 |
| 2002/0151939 A1 | 10/2002 | Rezai |
| 2003/0181954 A1 | 9/2003 | Rezai |
| 2003/0236558 A1 | 12/2003 | Whitehurst et al. |
| 2004/0015205 A1 | 1/2004 | Whitehurst et al. |
| 2004/0167583 A1 | 8/2004 | Knudson et al. |
| 2004/0172085 A1 | 9/2004 | Knudson et al. |
| 2004/0172088 A1 | 9/2004 | Knudson et al. |
| 2004/0172091 A1 | 9/2004 | Rezai |
| 2005/0021092 A1 | 1/2005 | Yun et al. |
| 2005/0021103 A1 | 1/2005 | DiLorenzo |
| 2005/0021104 A1 | 1/2005 | DiLorenzo |
| 2005/0038484 A1 | 2/2005 | Knudson et al. |
| 2005/0060010 A1 | 3/2005 | Goetz |
| 2005/0065562 A1 | 3/2005 | Rezai |
| 2005/0065573 A1 | 3/2005 | Rezai |
| 2005/0119703 A1 | 6/2005 | DiLorenzo |
| 2005/0131485 A1 | 6/2005 | Knudson et al. |
| 2005/0131506 A1 | 6/2005 | Rezai et al. |
| 2006/0009815 A1 | 1/2006 | Boveja |
| 2006/0020292 A1 | 1/2006 | Goetz |
| 2006/0095081 A1 | 5/2006 | Zhou et al. |

OTHER PUBLICATIONS

Bohning, D.E. et al., "Feasibility of Vagus Nerve Stimulation-Synchronized Blood Oxygenation Level-Dependent Functional MRI," Investigative Radiology, vol. 36, No. 8, (Aug. 2001), pp. 470-479.

Clark, K.B., et al., "Posttraining Electrical Stimulation of Vagal Afferents With Concomitant Vagal Efferent Inactivation Enhances Memory Storage Processes in the Rat," Neurobiology of Learning and Memory 70, Article No. NL983863, (1998) pp. 364-373.

Hallowitz, R.A., et al., "Effects of Vagal Volleys on Units of Intralaminar and Juxtalaminar Thalamic Nuclei in Monkeys," Brain Research, 130, (1977), pp. 271-286.

Koo, Betty, "EEG Changes With Vagus Nerve Stimulation," Journal of Clinical Neurophysiology, vol. 18, No. 5, (Sep. 2001), pp. 434-441.

Lockard, J.S., et al., "Feasibility and Safety of Vagal Stimulation in Monkey Model," Epilepsia, 31, (Suppl.2), (1990), pp. S20-S26.

Terry, R.S., et al., "The Implantable Neurocybernetic Prosthesis System," Pacing and Clinical Electrophysiology, vol. 14, No. 1, (Jan. 1991), pp. 86-93.

Vonck, K., et al., "The Mechanism of Action of Vagus Nerve Stimulation for Refractory Epilepsy," Journal of Neurophysiology, vol. 18, No. 5, (Sep. 2001), pp. 394-401.

Woodbury, J.W., et al., "Vagal Stimulation Reduces the Severity of Maximal Electroshock Seizures in Intact Rats: Use of Cuff Electrode for Stimulating and Recording," PACE, vol. 14, (Jan. 1991), pp. 94-107.

Zabara, J., "Inhibition of Experimental Seizures in Canines by Repetitive Vagal Stimulation," Epilepsia, 33(6), (1992), pp. 1005-1012.

* cited by examiner

IMPLANTABLE MEDICAL DEVICE HAVING MULTIPLE ELECTRODE/SENSOR CAPABILITY AND STIMULATION BASED ON SENSED INTRINSIC ACTIVITY

BACKGROUND

1. Technical Field

The disclosed subject matter relates generally to implantable medical devices and more particularly to implantable medical devices that are adaptable to one or more physiological conditions in a patient in which the devices are implanted.

2. Background Information

Various diseases and disorders of the nervous system are associated with abnormal neural discharge patterns. One treatment regimen for such diseases and disorders includes drug therapy. Another treatment technique includes the implantation in the patient of an implantable medical device that comprises a pulse generator for electrically stimulating a target location of the patient's neural tissue. In one such available treatment for epilepsy, the vagus nerve is electrically stimulated by a neurostimulator device substantially as described in one or more of U.S. Pat. Nos. 4,702,254, 4,867,164, and 5,025,807, all of which are incorporated herein by reference.

Some implantable pulse generators used for electrical stimulation of neurological tissue operate according to a therapy algorithm programmed into the device by a health care provider such as a physician. One or more parameters of the therapy may thereafter be changed by reprogramming the neurostimulator after implantation by transcutaneous communication between an external programming device and the implanted neurostimulator. The ability to program (and later re-program) the implanted device permits a health care provider to customize the therapy provided by the implanted device to the patient's needs, and to update the therapy periodically should those needs change.

It is desirable, however, for an implantable medical device, such as a neurostimulator, to be able to automatically detect the onset of one or more physiological parameters, particularly where the parameter(s) indicate the actual or impending occurrence of an undesirable physiological event, such as an epileptic seizure, and then initiate a therapeutic response specifically tailored to the physiological parameters detected in the body of the individual patient to mitigate or prevent the physiological event without the necessity of intervention by a health care provider. Detection of such physiological events is, however, complicated by physiological differences among patients. Improvements in this area are desirable.

BRIEF SUMMARY

Various apparatus and method embodiments of the invention are described herein. For example, in one embodiment of the invention, an implantable neurostimulator comprises a pulse generator that generates an electrical pulse signal to stimulate a neural structure in a patient, a stimulation lead assembly coupled to the pulse generator for delivering the electrical pulse signal to the neural structure, a plurality of sensors coupled to the pulse generator, and sensor select logic. Each sensor is individually selectable and the sensor select logic selects any two or more of the plurality of sensors for sensing a voltage difference between the selected sensors.

In another embodiment, an implantable neurostimulator comprises a pulse generator that generates an electrical pulse signal to stimulate a cranial nerve in a patient, a stimulation lead assembly, and a plurality of sensor elements. The sensor elements may be coupled to the pulse generator and sense at least two physiological parameters selected from the group consisting of an action potential in a nerve tissue, a heart parameter, a temperature, a blood parameter, and brain wave activity.

In yet another embodiment, an implantable neurostimulator comprises a pulse generator, a stimulation lead assembly, a plurality of sensor elements coupled to the pulse generator for sensing at least two physiological parameters selected from the group consisting of an action potential in a nerve tissue, a heart parameter, a temperature, a blood parameter, and brain wave activity, each of the sensor elements adapted to provide a sensor signal, and a controller. The controller receives and analyzes sensor signals from the sensor elements. The pulse generator generates the electrical pulse signal to provide therapeutic neurostimulation to the patient in response to the controller's analysis.

In another embodiment, a method comprises receiving sensor signals from at least two sensors in a patient and performing an analysis based on the at least two sensor signals to determine whether electrical neurostimulation is needed. The method further comprises providing an electrical pulse to a nerve in the patient when it is determined that electrical neurostimulation is needed.

In yet another embodiment, a method comprises sensing at least two physiological parameters selected from the group consisting of voltage fluctuations in a nerve tissue, a heart parameter, a temperature, a blood parameter, and brain wave activity. The method also comprises performing an analysis based on the at least two sensed physiological parameters to determine whether electrical neurostimulation is needed and providing an electrical pulse to a nerve in the patient when it is determined that electrical neurostimulation is needed.

In yet another embodiment, a method (and associated apparatus) comprises sensing intrinsic electrical activity on a person's nerve and stimulating the nerve based on the sensed intrinsic electrical activity of the nerve. This embodiment may be for either blocking intrinsic electrical activity from reaching the brain or to increase the efficacy of vagus nerve stimulation.

These and other embodiments are disclosed herein. The preferred embodiments described herein do not limit the scope of this disclosure.

NOTATION AND NOMENCLATURE

Certain terms are used throughout the following description and claims to refer to particular system components. Persons skilled in the art will appreciate that components may be denoted in the art by different names. The present invention includes within its scope all components, however denoted in the art, that achieve the same function. In the following discussion and in the claims, the terms "including" and "comprising" are used in an open-ended fashion, and thus should be interpreted to mean "including, but not limited to." Also, the terms "couple," "couples" or "coupled" are intended to refer to either an indirect or direct connection. Thus, if a first device couples to a second device, that connection may be through a direct connection, or through an indirect connection via other devices and connections.

BRIEF DESCRIPTION OF THE DRAWINGS

For a more detailed description of the preferred embodiments of the present invention, reference will now be made to the accompanying drawings, wherein.

DETAILED DESCRIPTION OF THE PREFERRED EMBODIMENTS

The present invention is susceptible to implementation in various embodiments. The disclosure of specific embodiments, including preferred embodiments, is not intended to limit the scope of the invention as claimed unless expressly specified. In addition, persons skilled in the art will understand that the invention has broad application. Accordingly, the discussion of particular embodiments is meant only to be exemplary, and does not imply that the scope of the disclosure, including the claims, is limited to specifically disclosed embodiments.

Figure 1:
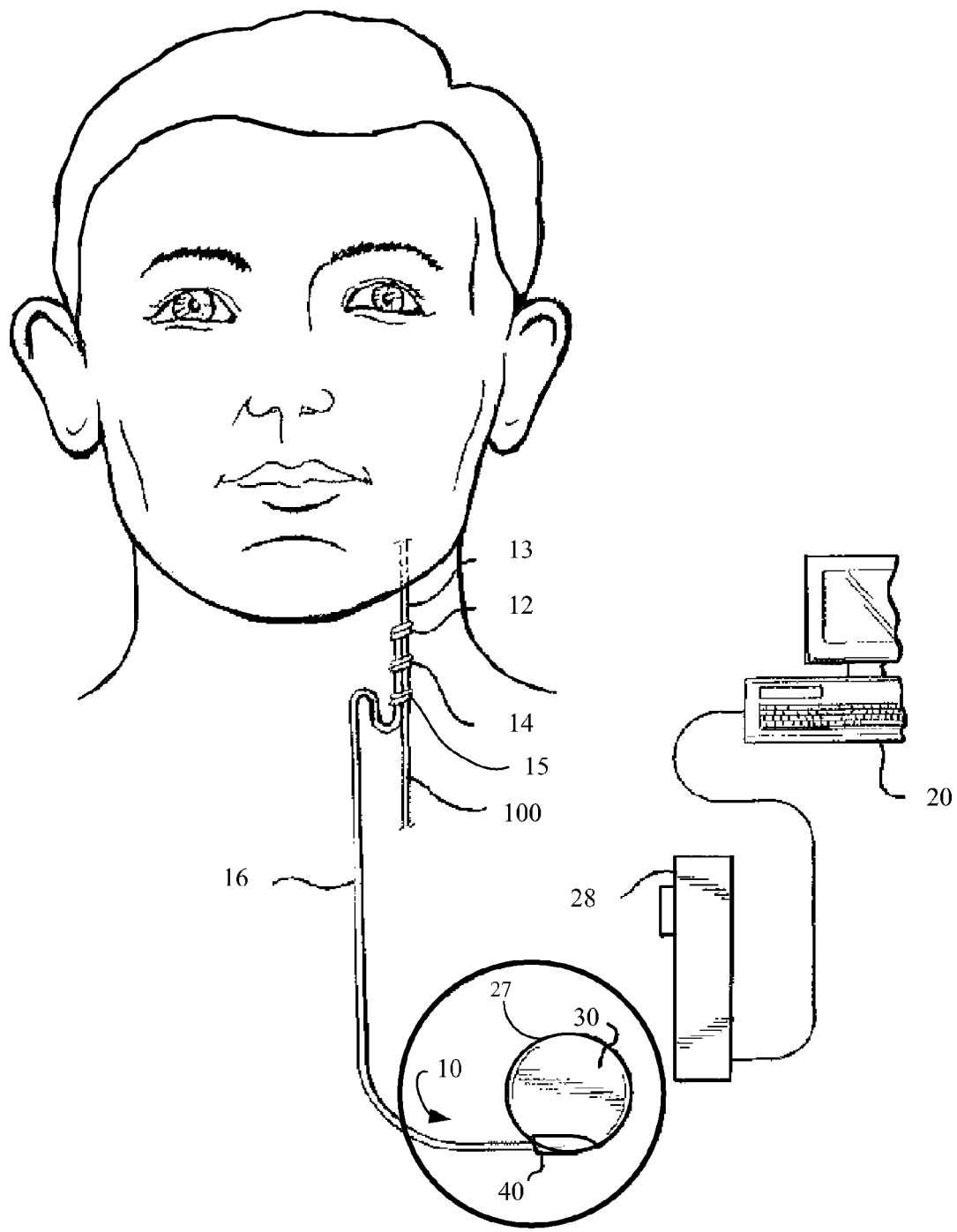
FIG. 1 depicts, in schematic form, an implantable medical device, in accordance with a preferred embodiment of the invention, implanted within a patient and programmable by an external programming system.

FIG. 1 illustrates an implantable medical device ("IMD") 10 implanted in a patient. The IMD 10 may be representative of any of a variety of medical devices. At least one preferred embodiment of the IMD 10 comprises a neurostimulator for stimulating a neural structure in a patient, particularly a neurostimulator for stimulating a patient's cranial nerve such as a vagus nerve 13. Although the device 10 is described below in terms of vagus nerve stimulation ("VNS"), the disclosure and claims that follow are not limited to VNS, and may be applied to the stimulation of other cranial nerves such as the trigeminal and/or glossopharyngeal nerves, or to other neural tissue such as one or more brain structures of the patient, spinal nerves, and other spinal structures.

Referring still to FIG. 1, a lead assembly comprising one or more leads 16 is coupled to the IMD 10 and includes one or more electrodes, such as electrodes 12 and 14. Each lead has a proximal end that connects to the IMD 10 and a distal end on which one or more electrodes are provided. At least one electrode, and preferably an electrode pair, is used as a stimulating electrode to deliver electrical current to target tissues such as the patient's vagus nerve 13. Further, at least one electrode (preferably an electrode pair) is used a sensing electrode to detect the electrical activity of target tissue (e.g., the vagus nerve).

In some embodiments, the stimulating electrode(s) is separate from the sensing electrode(s). In other embodiments, the same electrode can function both to stimulate and sense. Further still, some embodiments include a combination of stimulation-only electrodes, sensing-only electrodes, and combination stimulation and sensing electrodes. The number of stimulation-capable, sensing-capable, and the total number of electrodes can be selected as desired for the given application. An example of an electrode suitable for coupling to a vagus nerve to provide VNS therapy to a patient is disclosed in U.S. Pat. No. 4,979,511, incorporated herein by reference. Mechanism 15 comprises an attachment mechanism that attaches the lead assembly 16 to the vagus nerve to provide strain relief and is described in U.S. Pat. No. 4,979,511, incorporated herein by reference.

In addition to one or more electrodes attached to the patient's vagus nerve, one or more additional electrodes can also be provided and connected to IMD 10. Such other electrodes can function as sensing electrodes to sense any target parameter in the patient's body. For example, an electrode may be coupled to the patient's heart to sense the electrical activity of the heart. Sensing electrodes may be additionally or alternatively attached to other tissues of the body in addition to, or instead of, the patient's heart 17. In some embodiments, sensors besides electrodes can be included to sense various parameters of the patient. The term "sensor" is used herein to encompass both electrodes and other types of sensing elements. Sensors used in conjunction with IMD 10 may comprise electrodes that sense an electrical signal (e.g., a voltage indicative of cardiac or brain wave activity), a pressure transducer, an acoustic element, a photonic element (i.e., light emitting or absorbing), a blood pH sensor, a blood pressure sensor, a blood sugar sensor, a body movement sensor (e.g., an accelerometer), or any other element capable of providing a sensing signal representative of a physiological body parameter. Any of a variety of suitable techniques can be employed to run a lead from an implantable device through a patient's body to an attachment point such as the vagus nerve or cardiac or other tissue. In some embodiments, the outer surface of the IMD 10 itself may be electrically conductive and function as a sensor as well. As will be explained below, in at least some embodiments, the IMD 10 comprises logic by which any two or more sensors can be selected for operation with the IMD.

FIG. 1 also illustrates an external device implemented as a programming system 20 for the IMD 10. The programming system 20 comprises a processing unit coupled to a wand 28. The processing unit 24 may comprise a personal computer, personal digital assistant (PDA) device, or other suitable computing device consistent with the description contained herein. Methods and apparatus for communication between the IMD 10 and an external programming system 20 are known in the art. Representative techniques for such communication are disclosed in U.S. Pat. No. 5,304,206, and U.S. Pat. No. 5,235,980, both incorporated herein by reference. As explained below, the IMD 10 includes a transceiver (such as a coil) that permits signals to be communicated wirelessly between the wand 28 and the IMD 10. Via the wand 28, the programming system 20 generally monitors the performance of the IMD and downloads new programming information into the device to alter its operation as desired. The programming system 20 can also cause the IMD 10 to perform one or more calibration processes such as those described below.

Figure 2:
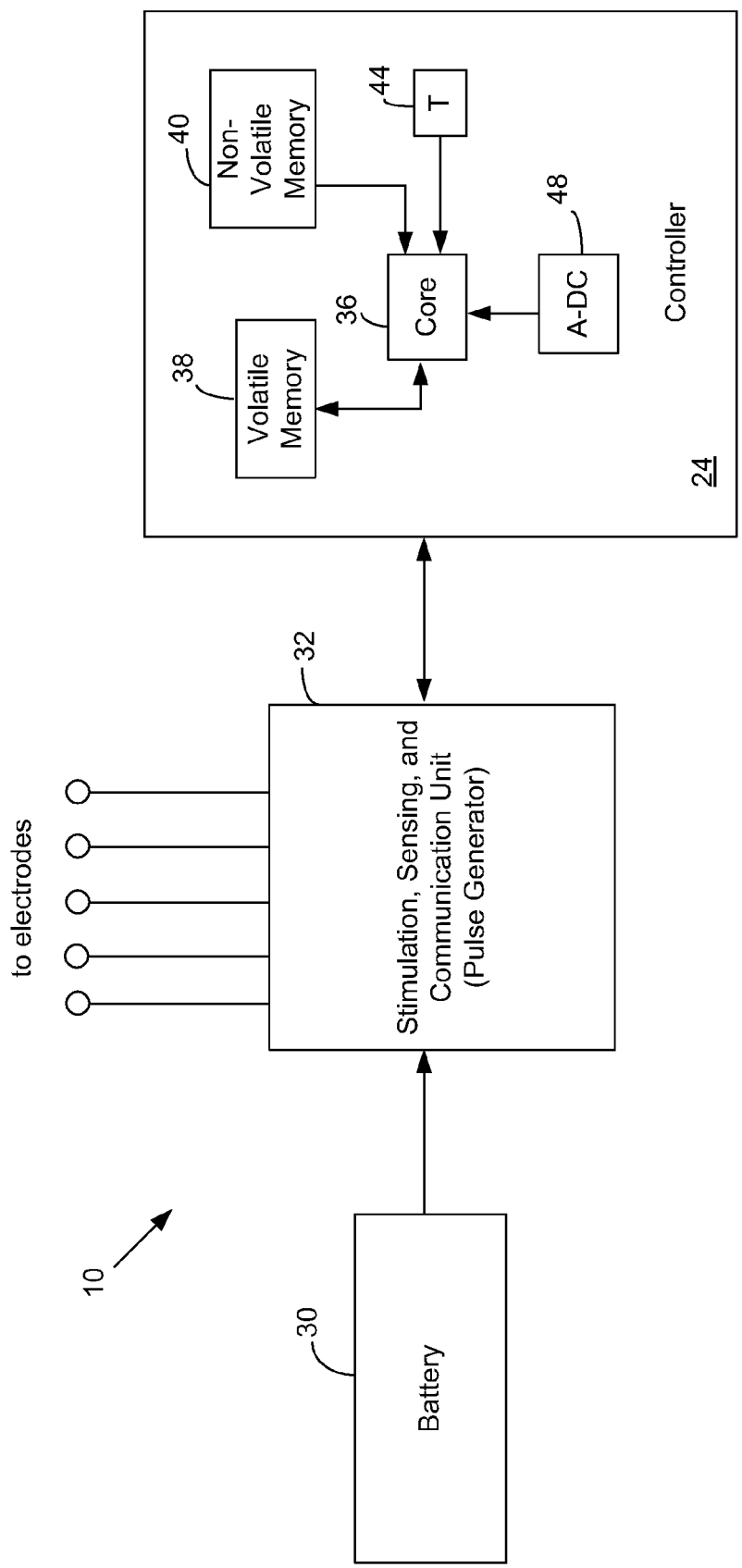
FIG. 2 is a block diagram of the implantable medical device of FIG. 1 and comprising a stimulation, sensing and communication unit.

FIG. 2 shows a block diagram of a preferred embodiment of the IMD 10. As shown, the IMD 10 includes a battery 30, a stimulation, sensing, and communication unit ("SSCU") 32, and a controller 34. The SSCU 32 may comprise, or be referred to as, a "pulse generator" or perform some or all of the functionality of a pulse generator. For example, under the control of controller 34 the SSCU 32 may generate an electrical pulse to stimulate a neural structure in a patient. The battery 30 provides power for both by the SSCU 32 and the controller 34. As explained in greater detail with respect to FIG. 3, the SSCU 32 includes a voltage regulator 58 that receives voltage from the battery 30 and provides operating voltage for use by the controller 34. In this way, the SSCU 32 can control the voltage provided to the controller 34. The controller 34 generally assists, controls, and/or programs the SSCU 32. Controller 34 preferably comprises a processor such as a low-power, mixed-signal microcontroller, such as a processor available from Texas Instruments, Inc. as the MSP430F148 processor. Other suitable controllers may be used, although the processor preferably is capable of processing a variety of sensor inputs, uses low power, and operates at a high speed. In general, however, any suitable processor can be used to implement the functionality performed by the controller 34 as explained herein. It will be appreciated that some features of the controller 34 may also be provided in whole or in part by the SSCU 32, and vice versa. Thus, while certain features of the present invention may be described as comprising part of the SSCU 32, it is not intended thereby to preclude embodiments in which the features are provided by the controller. Likewise, certain features described herein as comprising part of the controller 34 are not intended to preclude embodiments in which the features comprise part of the SSCU 32.

Figure 3:
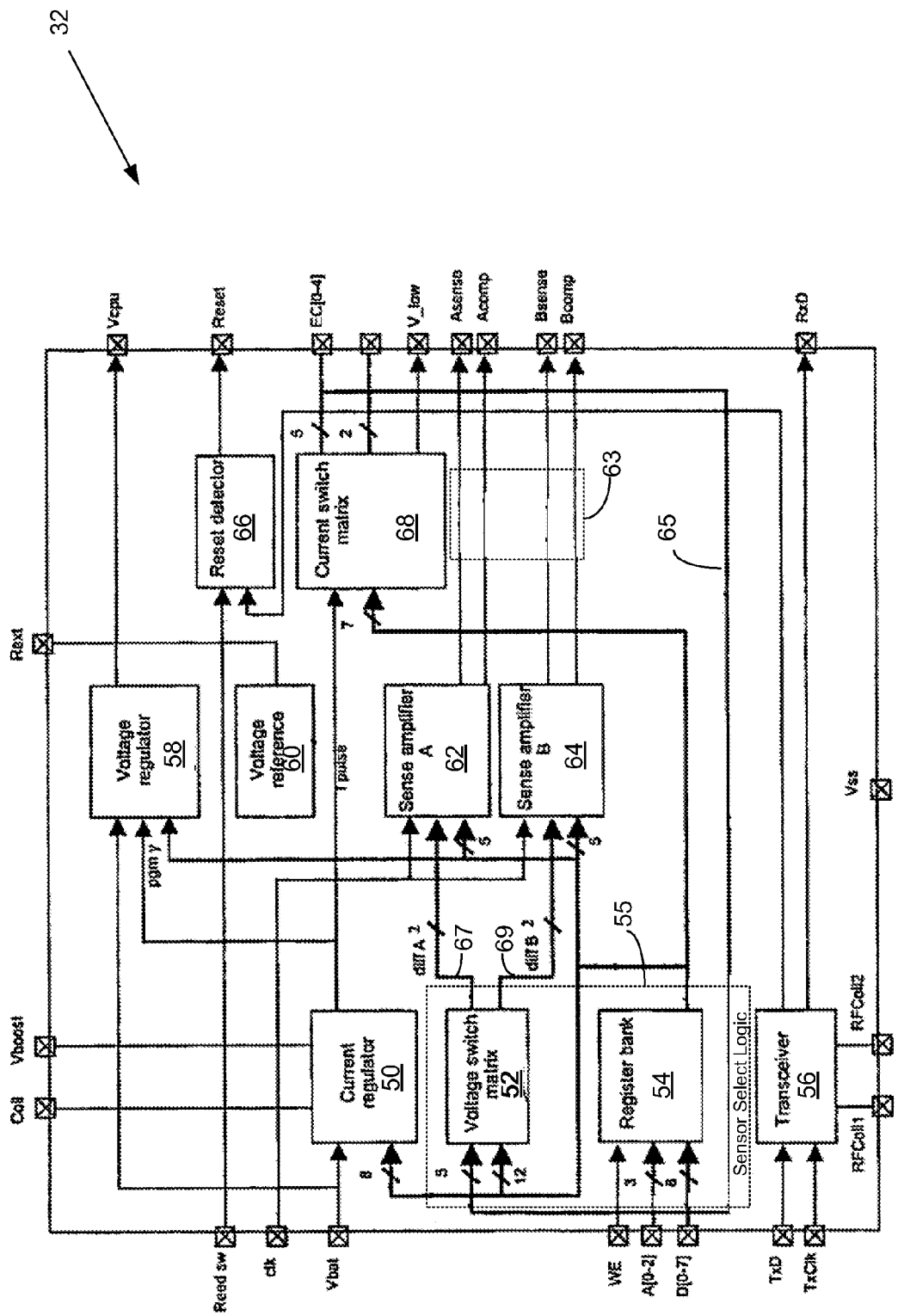
FIG. 3 is a block diagram of the stimulation, sensing and communication unit of FIG. 2.

FIG. 3 is a block diagram showing a preferred embodiment of the SSCU 32 depicted in FIG. 2. Although a particular architecture for SSCU 32 is provided in FIG. 3 and discussed more fully hereafter, the recitation of a particular architecture is not intended to limit the scope of the invention, which is limited only by the claims. The SSCU 32 comprises a current regulator 50, a voltage switch matrix 52, a register bank 54, a transceiver 56, a voltage regulator 58 (previously noted), a voltage reference 60, a pair of sense amplifiers 62 and 64, a reset detector 66, and a current switch matrix 68. The aforementioned components preferably are coupled together on a single integrated circuit chip as shown, but may also be implemented with other suitable architectures, including individual components or modules, although in general, integration of the components in a small number of modules increases reliability and reduces cost.

In accordance with the embodiment of FIG. 3, the register bank 54 comprises eight control registers. Each register includes eight bits, and the function performed by each register in the FIG. 3 embodiment is described below in Table I. The control registers are generally readable and writeable by the controller 34 to control the operation of the SSCU 32. Control information provided by the controller 34 to the SSCU 32 over the eight data lines (shown in FIG. 3 as "D[0-7]") is latched, upon detection of a rising edge of the write enable ("WE") signal, into the eight bits of the particular SSCU register that corresponds to the address provided on the three address signals ("A[0-2]"). Thus, the controller 34 is used to program the registers in the register bank 54 by providing data to be written on the data lines D0-D7, an address corresponding to the target register on the address lines A0-A2, and then asserting the WE signal to cause the target register to be programmed. Each of the eight registers is individually programmable by this process. The register bank 54 also converts the register data received from the controller 34 into one or more digital signals that are used by other components within the SSCU 32 as explained in greater detail below.

The eight registers of the register bank 54 are described below in Table I for a particular embodiment of the present invention.

TABLE I

REGISTER DESCRIPTIONS

| Register Name | Description |
| --- | --- |
| General Control | Controls the reset for the SSCU 32, bandgap trim for the sense amplifiers 62, 64 and trims for other functions |
| Voltage Control | Enables and controls the amount voltage boost (50) for current control, controls controller power (58) |
| Current Level | Controls the current output level (50) |
| Current Direction | Designates which electrodes function as cathode and anode for current pulse delivery (68), enables electrode discharge and reed switch bypass |
| Sense A Control | Controls operation of sense amp A (62) |
| Sense B Control | Controls operation of sense amp B (64) |
| Sense A Select | Selects positive and negative electrodes via switch matrix 52 for sense amp A (62) |
| Sense B Select | Selects positive and negative electrodes via switch matrix 52 for sense amp B (64) |

In preferred embodiments, the IMD 10 provides enhanced energy conservation by enabling two modes of operation for controller 34: a fully operational mode of operation and a lower power, standby mode to conserve battery power. In the fully operational mode of operation, the controller 34 preferably performs some, or all, of the functions described herein. In the standby mode, the controller 34 generally performs fewer functions than in the fully operational mode. In some embodiments, other than perhaps refreshing any internal memory contained in the controller, the standby mode generally limits the controller to wait for a transition to the fully operational mode. Because the controller is generally idle in the standby mode, battery power is conserved.

The controller 34 preferably includes, or otherwise accesses, a re-programmable memory such as flash memory (implemented as non-volatile memory 40 in FIG. 2) that preferably stores the software to be executed by the controller 34. The voltage required for the controller 34 to re-program its flash memory may be different than the voltage needed for the controller during other aspects of the fully operational mode. The voltage regulator 58 in the SSCU 32 receives voltage from the battery 30 and provides supply voltage for the controller 34 in the fully operational and standby modes of operation, as well as for programming flash memory contained in the controller.

The transceiver 56 generally permits the external wand 28 to communicate with the IMD 10. More particularly, transceiver 56 permits the external programming system 20 to program the IMD 10 (i.e., send program parameters to the IMD 10) and to monitor its configuration and state (i.e., query and receive signals from the IMD 10). In addition, transceiver 56 also permits the external programming system 20 (or the patient alone by a suitable signaling means such as a magnet) to inform the implantable IMD 10 of the occurrence of a physiological event such as a seizure.

In one embodiment, the SSCU 32 and the controller 34 preferably are reset on initial power-on or if the IMD simultaneously detects both a magnetic field and an RF transmission. Whenever a magnetic field is detected by a Reed switch (not specifically shown) in the IMD 10, all current switches within the VNS 10 are turned off as a safety precaution. This safety precaution can be temporarily overridden (i.e., the IMD 10 may continue to generate and deliver electrical pulses to stimulating electrode 14) by writing an override bit in the Current Direction register (listed in Table I). To protect against a "stuck at override" failure, the aforementioned override bit preferably resets itself after triggering an override time interval implemented by the reset detector 66.

The current regulator 50 delivers an electrical current programmed by the controller 34 to the patient via lead 16 and stimulating electrodes 12, 14. The IMD 10 preferably provides a constant current, used herein to refer to providing a predetermined current or pulse shape that is independent of the impedance across the leads (i.e., the impedance presented by the patient's tissues). To overcome this impedance, the current regulator 50 increases the battery voltage to a voltage that is determined by a value programmed into the Voltage Control register (Table I), while maintaining the current at a controlled magnitude. The magnitude of the current delivered to the patient also is programmable by programming system 20 and controller 34 by writing a desired value into the Current Level register (Table I).

The current switch matrix 68 preferably provides current from current regulator 50 to any desired sensor (e.g., electrodes) among those provided in IMD 10 as programmed by the controller 34. Where electrodes are used as the sensing elements, a voltage signal from the selected electrodes is provided for conversion from analog to digital form by the controller 34 (which preferably has one or more internal analog-to-digital converters 48, FIG. 2). The sense amplifiers 62 and 64 are used to detect electrophysiologic signals preferably in any desired frequency range such as from 1 to 100 Hz. The voltage switch matrix 52 connects the sense amplifiers 62 and 64 to any two or more selectable electrodes. The controller 34 can program the Sense A Select and Sense B Select registers in the register bank 54 to specify the particular sensor(s) that are selected to be coupled to each sense amplifier. The sensors selected may comprise two or more sensors provided on a single lead (e.g., lead 16, 18) or two or more sensors provided on different leads. The selected sensors may also comprise a sensor provided on a lead and an electrically conductive portion of the outer surface (sometimes referred to as the "can") of the IMD 10, which may also be used as an electrode. Thus, in accordance with at least some embodiments, voltage switch matrix 52 and register bank 54 in conjunction with the controller 34, comprise sensor select logic 55 which can be used to select any two or more sensors for sensing a voltage difference between the selected sensors.

The detection threshold of each sense amplifier 62, 64 is individually programmable, preferably in logarithmic steps, by the controller 34 writing to the General Control register (Table I) of register bank 54. If a differential input signal exceeds the threshold, a digital output is asserted by the connected sense amplifier. If not needed, the sense amplifiers can be switched off to a lower-power mode (also via the General Control register).

Referring still to FIG. 3, in accordance with a preferred embodiment of the invention, the IMD 10 is capable of sensing two or more physiologic parameters via two or more of the electrodes ("EC[0-4]"). Although five electrodes EC[0-4] are denoted in FIG. 3, it will be understood by persons of skill in the art that any number of electrodes may be included for sensing a variety of physiological parameters. Sensors may connected to one or more of the SSCU's electrode connections EC[0-4]. As described above, the sensors may comprise any of the following non-limiting examples: electrodes that sense electrical activity, a pressure transducer, an acoustic element, a photonic element, a blood pH sensor, a blood pressure sensor, a blood sugar sensor, or a body movement sensor. Accordingly, the sensors that are coupled to the IMD 10 are capable of sensing one or more, and preferably two or more, physiological parameters selected from the following exemplary list: an action potential in a nerve tissue, a heart parameter, a body temperature, a blood parameter (e.g., pH, pressure), and brain activity. The term "physiologic parameter" is intended to embrace all such parameters whether they originate as electrical or non-electrical signals. The controller 34 preferably programs the SSCU's register bank 54 to sense whichever physiological parameters are desired for the patient among the various sensors.

The sensed signals are received by the IMD 10 via one or more sensors. The controller 34 preferably programs the General Control register in the register bank 54 to activate either or both of the sense amplifiers 62 and 64 to receive signals from the sensors and/or electrodes. The signals from the sensors are routed via conductors 65, through the voltage switch matrix 52 (programmed as explained above) and via the differential input conductors 67 and 69 to either or both of the sense amplifiers 62 and 64. The output signals 63 from the sense amplifiers 62 and 64 are provided to the controller 34 and converted into digital form by an analog-to-digital converter (ADC) 48 in the controller as noted above. The controller 34 then can analyze and process the received signals in accordance with the programming of the controller as explained below.

In some embodiments, the IMD 10 is programmed to deliver a stimulation therapy (e.g., vagus nerve stimulation) at programmed time intervals (e.g., every five minutes) without regard to the physical condition of the patient, time of day, or other variables that may influence the need for, and/or efficacy of, the stimulation. Such a treatment regimen is referred to as "passive stimulation." Alternatively or additionally, the implantable IMD 10 may be programmed to initiate a therapeutic response upon detection of a physiological event or upon another occurrence. Such responsive stimulation is referred to as "active stimulation." As such, the IMD 10 delivers a programmed therapy to the patient based on signals received from at least two sensors or based on at least two monitored physiological parameters. This disclosure is not limited to any particular type of physiological event. Non-limiting examples of a physiological event include an epileptic seizure and a cardiac arrhythmia. The IMD 10 thus permits at least two physiological parameters to be sensed. Based on the physiological parameters sensed or signals indicative of the sensed parameters, the IMD 10 performs an analysis using an analysis module, typically comprising software and/or firmware, to determine whether electrical neurostimulation is needed. If the analysis module determines that electrical neurostimulation is needed, then the IMD 10 provides an appropriate electrical pulse to a neural structure, preferably a cranial nerve. In the absence of a signal based on analysis by the analysis module, either passive stimulation or no electrical neurostimulation may be provided.

Physiological parameters that provide an indication of the physiological event generally vary from patient to patient. For example, action potentials on the vagus nerve during an epileptic seizure are detectable by measuring voltage fluctuations on the vagus nerve using a sensing electrode pair. The measured voltage fluctuations may differ among patients experiencing the same type of seizure. Similarly, body temperature measurements during a seizure may differ among patient having the same type of seizure. Accordingly, the IMD 10 can advantageously be adapted to the patient in which the IMD 10 is implanted. As explained below, the IMD 10 of the present invention can be customized to the particular patient's physiology to enable a more accurate physiologic event detection mechanism than might otherwise be possible.

Figure 4:
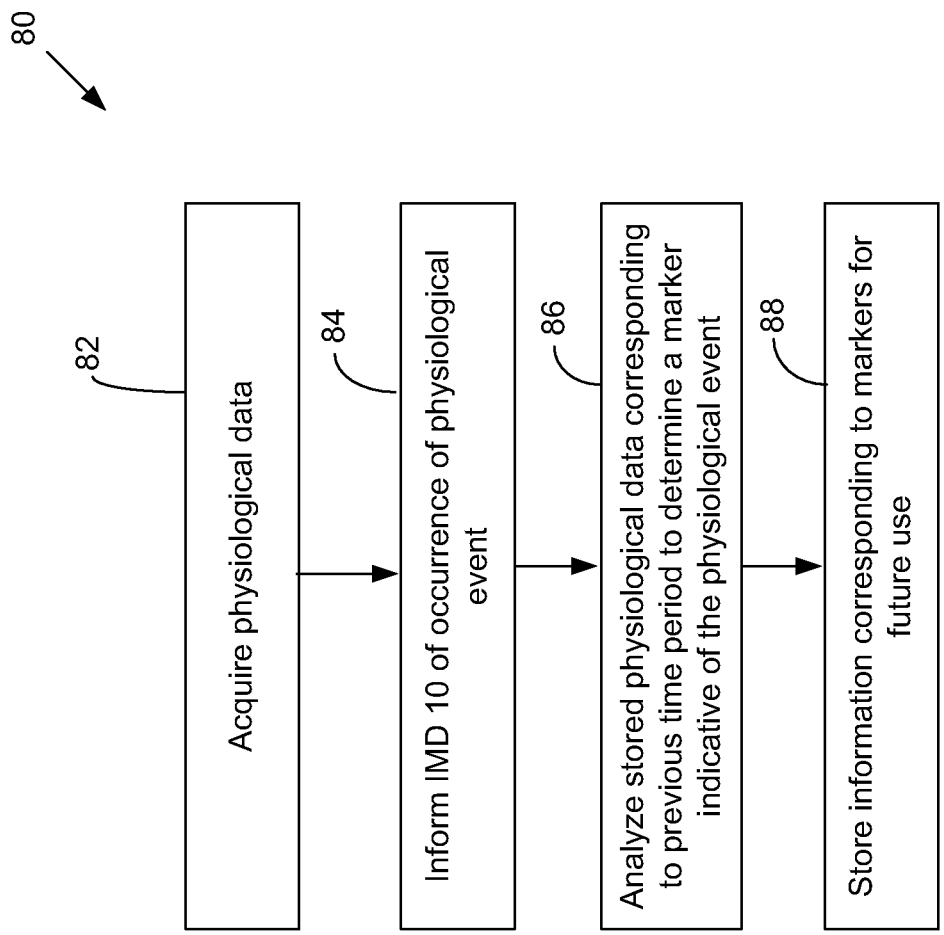
FIG. 4 is a flow chart depicting an exemplary method for determining one or more markers in a patient's physiologically parameters indicative of the occurrence or impending occurrence of a physiological event.

FIG. 4 illustrates a preferred method 80 for customizing the IMD 10 to the patient in which the IMD is implanted. During routine operation, at block 82 the controller 34 in the IMD 10 causes the IMD 10 to dynamically acquire data representing one or more, and preferably two or more, physiological parameters, such as those specified above. Dynamically acquiring physiological parameters comprises sensing the physiological parameters with a sensor, generating a first set of signals representative of the physiological parameters sensed over a first time period, and storing the first set of signals in a memory. Control logic is provided to facilitate the operation of the sensors, including the timing and sampling rate for each sensor. In block 84, method 80 further comprises informing the IMD 10 of the occurrence of the physiological event. This act includes determining when a physiological event has occurred in the patient and providing an indication of the occurrence of the event. The determination of the occurrence of the event may be made by the patient or a healthcare provider, or automatically by, for example, a program analyzing EEG data of the patient to confirm an epileptic seizure.

The IMD 10 may be informed of the physiologic event occurrence in accordance with any suitable technique. For example, the patient (or a healthcare provider) may inform the IMD 10 of the onset of the physiologic event by way of a predetermined signal received from the wand 28 of the external programming system 20. If the patient is not in the general vicinity of the external programming system when the physiological event occurs, the patient may place an external device (e.g., a portable magnet) generally over the site of the IMD 10 to trigger a Reed switch inside the IMD, thereby signaling to the IMD that the event has occurred. In still other embodiments, the IMD 10 may include an accelerometer that can detect a tap on the patient's skin over the site of the implanted IMD, and the event signal comprises the output signal from the accelerometer. In general, any mechanism by which the implanted IMD 10 can be informed of the occurrence of a physiologic event is acceptable. In some embodiments, the IMD is informed of the occurrence of the physiologic event at or near the beginning of the physiological event, or during or even after the physiological event.

Referring still to FIG. 4, at block 86, controller 34 analyzes the stored first set of signals that correspond to a time period n. The time period n can be any desired period of time but is preferably a period of time preceding a physiological event. In some embodiments, n may comprise any time period within a range of time periods such as approximately a five minute period of time preceding the point at which the IMD was informed of the occurrence of the physiological event by one of the methods previously described or other methods, such as the period from five minutes prior to the signal informing the IMD of the event until the signal itself. In another embodiment, the time period may comprise the period from 30 minutes prior to the signal to the signal. In still other embodiments, more than one time domain may be examined, such as the five-minute period preceding the signal and the period from one hour to 30 minutes preceding the signal. When only a single time domain is examined, the time period n is preferably programmable, which may be accomplished by the controller 34 writing to the General Control register in the register bank 54. The controller 34 analyzes the previously stored physiological data during the time period according to an algorithm 89 that determines one or more "markers" that may be indicative of either a precursor to the physiological event, or the physiological event itself. The markers may be unique to each patient. Such markers may include, but are not limited to, physiological data magnitudes, physiological data timing, physiological data frequency content, physiological data variability, correspondence of physiological data characteristics to stimuli, and combinations thereof. Once the controller 34 analyzes the stored physiological data and determines the marker(s) that are useful to detect future occurrences of the physiologic event, in block 88 information characteristic of the marker(s) preferably is stored in memory in the controller 34 and used to automatically detect future physiological event episodes by recognition of sensed data similar to the markers.

In accordance with other embodiments, blocks 86 and 88 may be performed by an external device that analyzes the patient's previously stored physiological data, such as a physiological event analysis program executing algorithm 89 in programming system 20. For example, in one such embodiment the implanted IMD 10 may be informed of the occurrence of a physiological event as described above. Thereafter, rather than having the implanted IMD itself determine the markers, the IMD may simply record a timestamp in the stored physiologic data stream to indicate when the physiologic event occurred. Subsequently, programming system 20 may upload the physiological data, including the physiological event timestamps, from the implanted IMD 10, and analyze the data for the time interval n prior to the timestamps, as described in blocks 86 and 88 of FIG. 4. In this embodiment, the programming system 20 contains a program or logic (e.g., a processor executing suitable software) to determine suitable markers for the patient based on the physiological data uploaded from the patient. Programming system 20 can then be used to download information corresponding to the determined markers into the implanted IMD 10 for storage and subsequent use by the IMD itself to determine future occurrences of the physiological event as exemplified in FIG. 5

Figure 5:
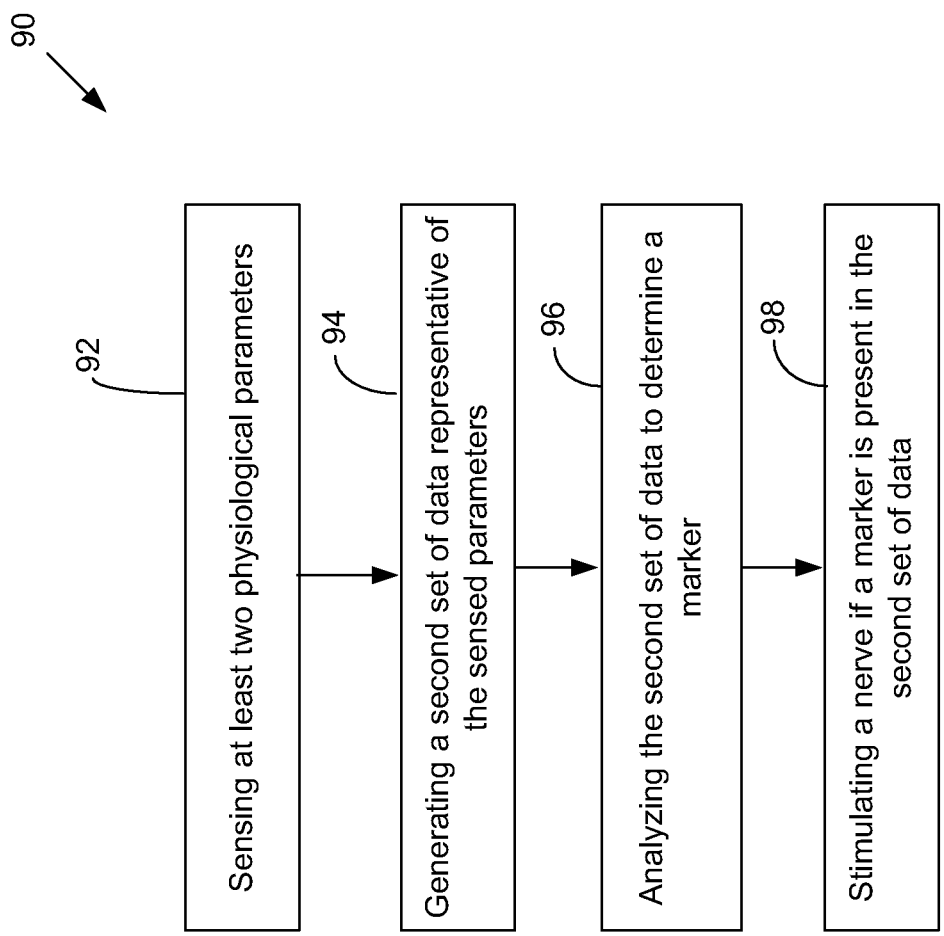
FIG. 5 is a flow chart illustrating the use of the marker(s) to predict or detect the onset of a physiological event.

FIG. 5 depicts a preferred method 90 for using the marker(s) generated in method 80 of FIG. 4. In block 92, the method comprises sensing at least two physiological parameters. In block 94, a second set (time series) of data is generated that is representative of the sensed parameters. This second set of data is then analyzed in block 96 to determine the presence of the marker(s) generated previously (FIG. 4). If a marker is found in the second set of data, a nerve is stimulated in accordance with a therapeutic response. The therapeutic response may be programmed into the IMD 10. In some embodiments, the IMD 10 may deliver a first programmed therapy (e.g., a predetermined stimulation therapy delivered at preset time intervals (e.g., every five minutes). When a marker is detected in the second set of data, the first programmed therapy can be delivered at that time rather than waiting for the next scheduled time interval. In other embodiments, the detection of the marker may cause a second therapy to be delivered that may be different than the first therapy. The second therapy may be based on the first therapy, but with one or more parameters (e.g., pulse amplitude, pulse shape, duration, etc.) altered from the first therapy. The second therapy may be delivered instead of the first therapy for the next scheduled interval (or more than one interval), or may be delivered in addition to the first therapy, although it is preferred that delivery of the first and second therapies not overlap in time.

The IMD 10 can be operated to provide therapy for one or more of a variety of diseases, disorders, or conditions including, without limitation, seizure disorders (e.g., epilepsy and Parkinson's disease), neuropsychiatric disorders including depression, schizophrenia, bi-polar disorder, borderline personality disorder, and anxiety, obesity, eating disorders including anorexia nervosa, bulimia, and compulsive over-eating, headaches (e.g., migraine headaches, neuromuscular headaches), endocrine disorders (e.g., disorders of the pituitary gland, thyroid gland, adrenal system, or reproductive system including pancreatic disorders such as diabetes and hypoglycemia), dementia including cortical, sub-cortical, multi-infarct, Alzheimer's disease, and Pick's disease, pain syndromes including chronic, persistent or recurring neuropathic or psychogenic pain, sleep disorders including sleep apnea, insomnia and hypersomnia including narcolepsy, sleep walking and enuresis, motility disorders (including hypermotility and hypomotility of the stomach, duodenum, intestines, or bowel), Crohn's disease, ulcerative colitis, functional bowel disorders, irritable bowel syndrome, colonic diverticular disease, coma, circulatory and/or coronary diseases (such as hypertension, heart failure, and heartbeat irregularities such as bradycardia and tachycardia).

In accordance with yet another embodiment of the invention, the IMD 10 preferably is configurable to provide a programmable and suitable therapy for any one or more diseases, disorders or conditions for which the IMD can provide therapy in response to sensed physiological parameters. At least some of the various medical problems that the IMD 10 can be programmed to address are disclosed in any one or more of the following United States patents, all of which are incorporated herein by reference: U.S. Pat. No. 4,702,254 ("Neurocybernetic Prosthesis"), U.S. Pat. No. 5,188,104 and U.S. Pat. No. 5,263,480 ("Treatment of Eating Disorders by Nerve Stimulation"), U.S. Pat. No. 5,215,086 ("Therapeutic Treatment of Migraine Symptoms by Stimulation"), U.S. Pat. No. 5,231,988 ("Treatment of Endocrine Disorders by Nerve Stimulation"), U.S. Pat. No. 5,269,303 ("Treatment of Dementia by Nerve Stimulation"), U.S. Pat. No. 5,299,569 ("Treatment of Neuropsychiatric Disorders by Nerve Stimulation"), U.S. Pat. No. 5,330,515 ("Treatment of Pain by Vagal Afferent Stimulation"), U.S. Pat. No. 5,335,657 ("Therapeutic Treatment of Sleep Disorder by Nerve Stimulation"), U.S. Pat. No. 5,540,730 ("Treatment of Motility Disorders by Nerve Stimulation"), U.S. Pat. No. 5,571,150 ("Treatment of Patients in Coma by Nerve Stimulation"), U.S. Pat. No. 5,707,400 ("Treating Refractory Hypertension by Nerve Stimulation"), U.S. Pat. No. 6,026,326 ("Apparatus and Method for Treating Chronic Constipation"), U.S. Pat. No. 6,473,644 ("Method to Enhance Cardiac Capillary Growth in Heart Failure Patients"), U.S. Pat. No. 6,587,719 ("Treatment of Obesity by Bilateral Vagus Nerve Stimulation"), and U.S. Pat. No. 6,622,041 ("Treatment of Congestive Heart Failure and Autonomic Cardiovascular Drive Disorders"). In this embodiment, the IMD 10 is programmed to detect the onset of a predetermined physiological event associated with the medical problem or condition afflicting the patient. The IMD 10 is also pre-programmed with a cranial nerve stimulation therapy, preferably a vagus nerve stimulation therapy, suitable for the patient's affliction. One or more detection modalities and therapeutic responses are described in one or more of the aforementioned patents incorporated herein by reference. Further, the IMD 10 can be customized to the physiological symptoms manifested by the patient as described above.

In still other embodiments, the IMD 10 can be programmed to provide therapy for a plurality of diseases, disorders, or conditions such as those listed above. The IMD 10 in this embodiment comprises a sufficient number of sensors, preferably comprising electrode pairs, to sense parameters indicting physiological events associated with a plurality of diseases, disorders, or conditions (generally referred to hereinafter as "medical conditions"). In this embodiment, the IMD is adapted to sense physiological parameters corresponding to a first physiological event associated with a first medical condition, and provide a suitable pre-programmed therapy in response (or prior to) the first physiological event, and also to sense one or more other physiological parameters corresponding to a second physiological event associated with a second medical condition, and provide a pre-programmed therapy suitable for the second medical condition. In this embodiment, the IMD may comprise controller 34 and SSCU 32. The controller 34 preferably is configurable to receive signals from a plurality of sensors, each corresponding to one or more physiological parameters indicative of one or more physiological events associated with one or more medical conditions experienced by a patient. Further, the controller 34 preferably analyzes sensor data to determine the impending onset of a physiological event (e.g., epileptic seizure, cardiac arrhythmia, indigestion, hunger, pain) and to cause the SSCU to provide a programmable therapy for each medical condition whose onset has been indicated (and/or diagnosed). The programmable therapy for each condition may be stored in memory in the controller 34.

Figure 6:
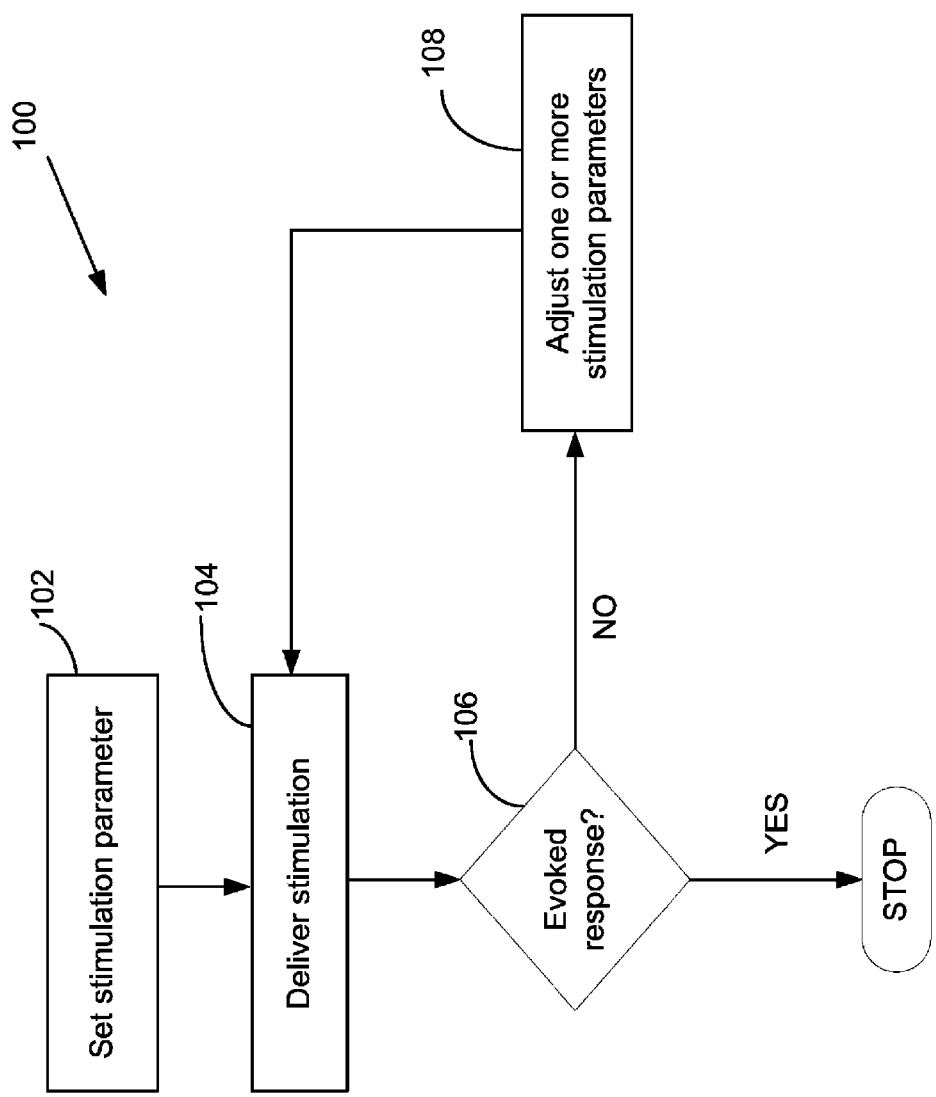
FIG. 6 is a flow chart illustrating an embodiment of adjusting one or more stimulation parameters to elicit an evoked response.

In accordance with another embodiment, FIG. 6 illustrates a method 100 for a calibration process that adjusts the stimulation produced by the IMD 10 to achieve a first evoked response from tissue. In one embodiment, IMD 10 comprises a neurostimulator for a cranial nerve (e.g., a vagus nerve) and the method comprises determining a first threshold that corresponds to minimum stimulation parameter settings sufficient to elicit a first evoked response from the cranial nerve. Minimum settings for stimulation parameters (e.g., current magnitude, frequency, pulse width, on-time and off-time) for the IMD 10 result in eliciting at least a first evoked response from the nerve while consuming relatively little power, or at least less power than for other configuration settings. Because changes in any of a number of stimulation parameters can affect the threshold for eliciting an evoked response, a number of "minimum settings" may be possible, as lower settings for one parameter may be offset by a higher setting for another parameter. Because the IMD 10 preferably is implanted in the patient and thus run from a battery source, minimizing or reducing power consumption is desirable to increase battery life.

The method of FIG. 6 illustrates a technique to determine the settings for the IMD 10 that cause the IMD to produce a stimulation that elicits a first evoked response from the vagus nerve, preferably while reducing or minimizing power consumption. The IMD settings determined according to the method of FIG. 6 may be used to determine both desired and undesired evoked responses. A desired response may comprise, for example, an evoked stimulation "floor" defining a "minimum parameter" set for stimulation of a cranial nerve such as a vagus nerve. An undesired response may comprise a pain threshold at which the patient feels pain resulting from the stimulation. Another undesired response may comprise retching by the patient. Responses such as pain or retching threshold are examples of stimulation "ceilings," i.e., an upper limit on one or more stimulation parameters, above which patient tolerance is minimal or absent. Optimum settings between "floor" and "ceiling" settings may also be determined by the method of FIG. 6.

Referring still to FIG. 6, method 100 may be performed during implantation of the IMD 10 in the patient or after implantation during a calibration mode of operation as effectuated by, for example, the programming system 20. For example, the method may be performed after implantation of the IMD 100 to establish new parameter settings if changes in the nerve have resulted in changes in stimulation thresholds such as the "floor" and "ceiling" thresholds previously discussed. At block 102, the method comprises setting values for the stimulation parameters such as current level, frequency, duration, etc. In the IMD 10 of FIG. 3, one or more of the parameters are programmable in the IMD 10 via register bank 54. In at least some embodiments, the parameters set in block 102 preferably are initially set so as to cause the IMD to produce a sufficiently low level of excitation energy to be unable to elicit an evoked response from the target vagus nerve.

Referring again to FIG. 6, in block 104 a stimulation is delivered by the IMD 10 to the vagus nerve in accordance with the parameters set in block 102. In decision block 106, the method determines whether an evoked response resulted from the stimulation of block 104. An evoked response can be determined via sensing electrodes placed on or near the vagus nerve and may either be distal to the stimulation electrodes or comprise the stimulation electrodes themselves. In other embodiments, the sensing electrodes may be at a different location on the nerve, such as in or near a final target region (e.g., the brain).

Regardless of the location of the sensing electrodes, IMD 10 receives the signals from the electrodes and determines whether an evoked response has occurred. The sensing data may be compared to a programmed threshold that corresponds to a minimum signal that corresponds to an effective induced action potential. The threshold may be based upon one or more of the sensed signal amplitude, time delay since the stimulation pulse, and/or signal frequency content. Alternatively, the threshold may comprise a minimum change in response to a stimulation change below which a change in stimulation does not produce an effective change in action potential. If an evoked response is determined to have occurred, then method 100 stops. Otherwise, the method comprises adjusting one or more of the stimulation parameters at 108 and repeating the actions of blocks 104 and 106. This process repeats itself until an evoked response is detected. Once an evoked response is detected, the most recent settings for the stimulation parameters are used to deliver future neurostimulation therapy.

Figure 7:
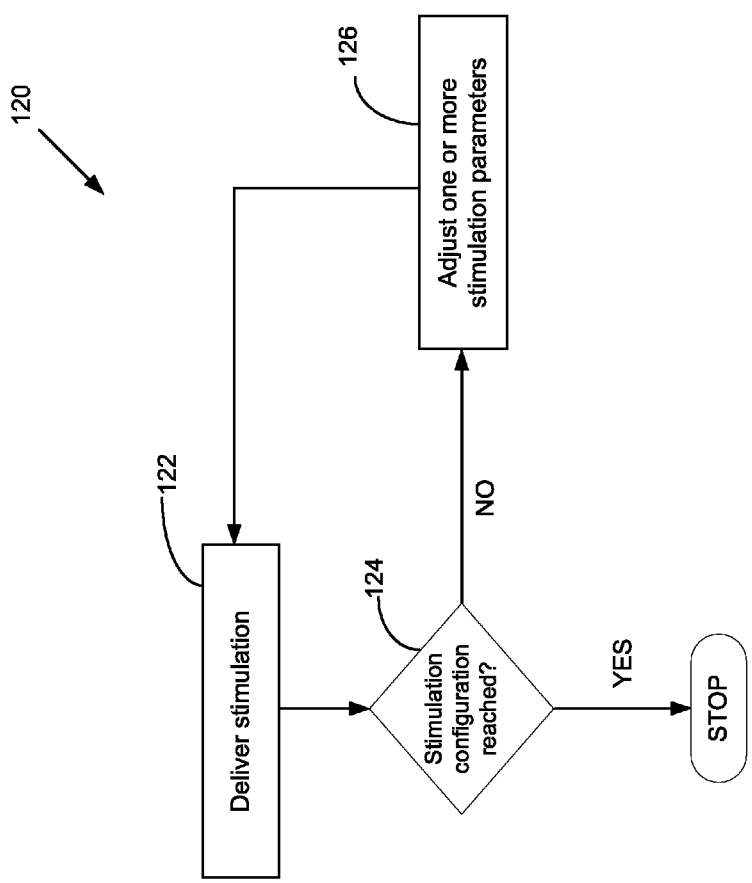
FIG. 7 is a flow chart illustrating an embodiment of adjusting one or more stimulation parameters to determine a stimulation ceiling for an evoked response.

FIG. 7 shows a method 120 for a calibration process in which stimulation parameters are determined to achieve a stimulation "ceiling." Induced action potentials on neurons within a nerve bundle such as the vagus nerve may increase as one or more stimulation parameter settings are increased until all effective neurons are activated, after which increases in stimulation are not beneficial (and may be detrimental). Method 120 ensures that stimulation is not above this maximum level (the "ceiling"). At levels above the ceiling, the IMD would be wasting energy, stimulating unwanted tissues, saturating desired tissues, and/or inducing discomfort or other unacceptable responses in the patient. Method 120 may be performed during implantation of the IMD 10 in the patient or after implantation during a calibration mode of operation as effectuated by, for example, the programming system 20.

After a stimulation is delivered at 122, a decision is made at 124 to determine whether the ceiling has been reached or exceeded. If the ceiling has been reached or exceed, the process stops. If the ceiling has not been reached or exceeded, the method comprises at 126 the step of adjusting one or more stimulation parameters (e.g., current magnitude, frequency, duration, etc.) and looping back to block 122. Once the process stops, the most recent settings for the stimulation parameters are used to deliver future neurostimulation therapy.

Figure 8:
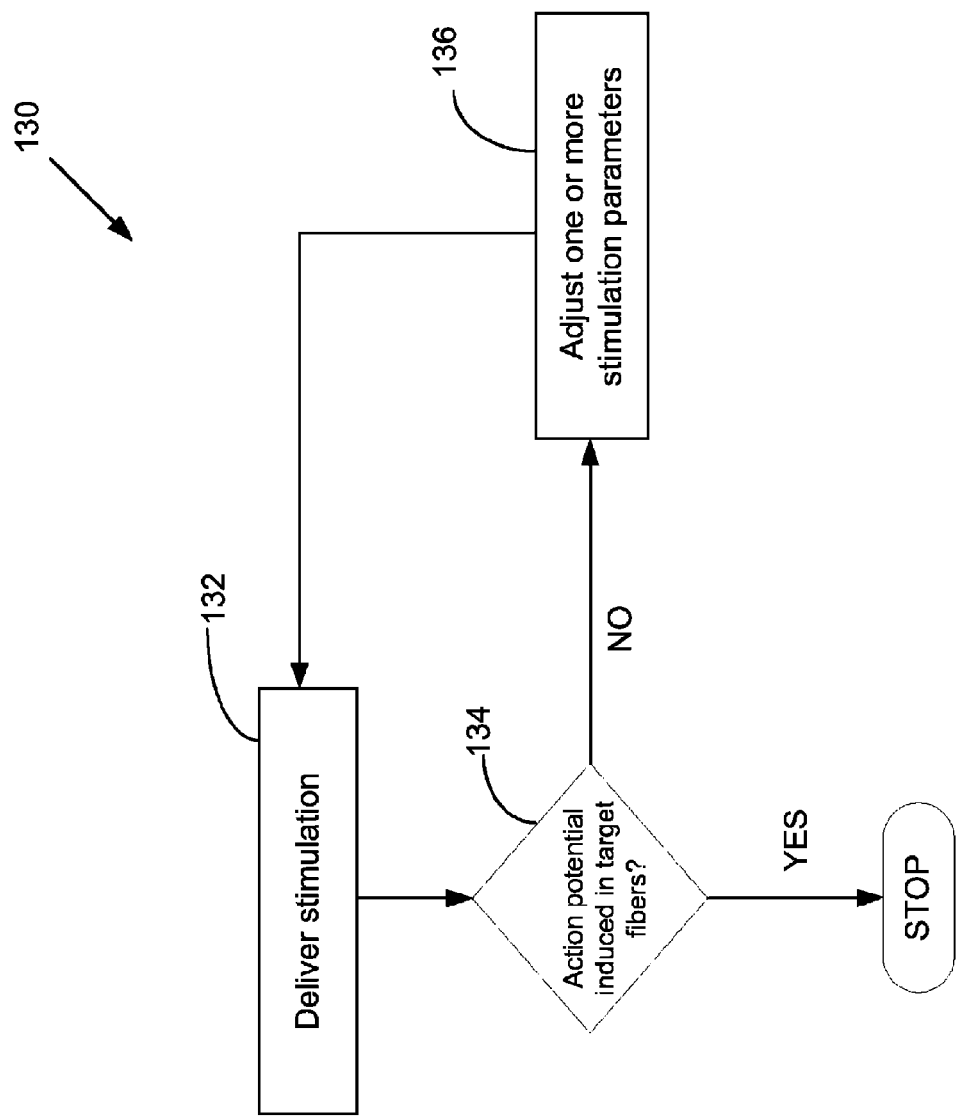
FIG. 8 is a flow chart illustrating an embodiment of adjusting one or more stimulation parameters to induce an action potential in one or more target vagus nerve fibers.

FIG. 8 shows a method 130 for a calibration process in which stimulation parameters are determined to target one or more specific types or sub-types of fibers within a nerve bundle. The vagus nerve, for example, comprises multiple nerve fibers (A fibers, B fibers, C fibers). By targeting one or more particular fibers for stimulation, and conversely not targeting one or more other fiber types, efficacy of neurostimulation therapy may be improved and/or side effects may be reduced. Different fiber types have different characteristics in their action potentials. As a result, the stimulation-induced action potentials may be monitored to determine what is being stimulated. Accordingly, method 130 permits the IMD 10 to be configured to adjust the stimulation to increase or maximize excitation of targeted fiber types, and/or reduce or minimize excitation of untargeted fiber types. In one nonlimiting example, stimulation parameters may be selected to stimulate only type A fibers, and avoid (or at least minimize) stimulation of type B and C fibers. Method 130 may be performed during implantation of the IMD 10 in the patient or after implantation during a calibration mode of operation as effectuated by, for example, the programming system 20. The programming system 20 can cause the calibration process of FIG. 8 to be performed for a specific fiber type as selected by a user of the programming system.

Referring again to FIG. 8, a stimulation is delivered to the nerve at 132. After the stimulation is delivered, a decision is made at 134 to determine whether action potentials have been induced in the target fiber type. This determination can be made in accordance with any of a variety of techniques. Any one or more of the following characteristics can be monitored using the sensing electrodes to determine whether the target fiber type has been excited: time delay from stimulation to detected excitation, time duration of the action potential, and frequency content of the action potential. A specific threshold, which may comprise a measured voltage response profile in the nerve over a target time interval following stimulation, can be set for any of the aforementioned characteristics and a comparison of the nerve signal to the thresholds can be made to determine whether the target fiber type has been excited. The specific thresholds used in this analysis may be set according to the specific fiber types being targeted. Accordingly, the thresholds may vary from application to application.

If the target fiber type(s) has been excited, the process stops. If the target fiber type(s) has not been excited, then at 136 the method comprises adjusting one or more stimulation parameters (e.g., current magnitude, frequency, duration, etc.) and looping back to block 132. Once the process stops, the most recent settings for the stimulation parameters are used to deliver future neurostimulation therapy.

Figure 9:
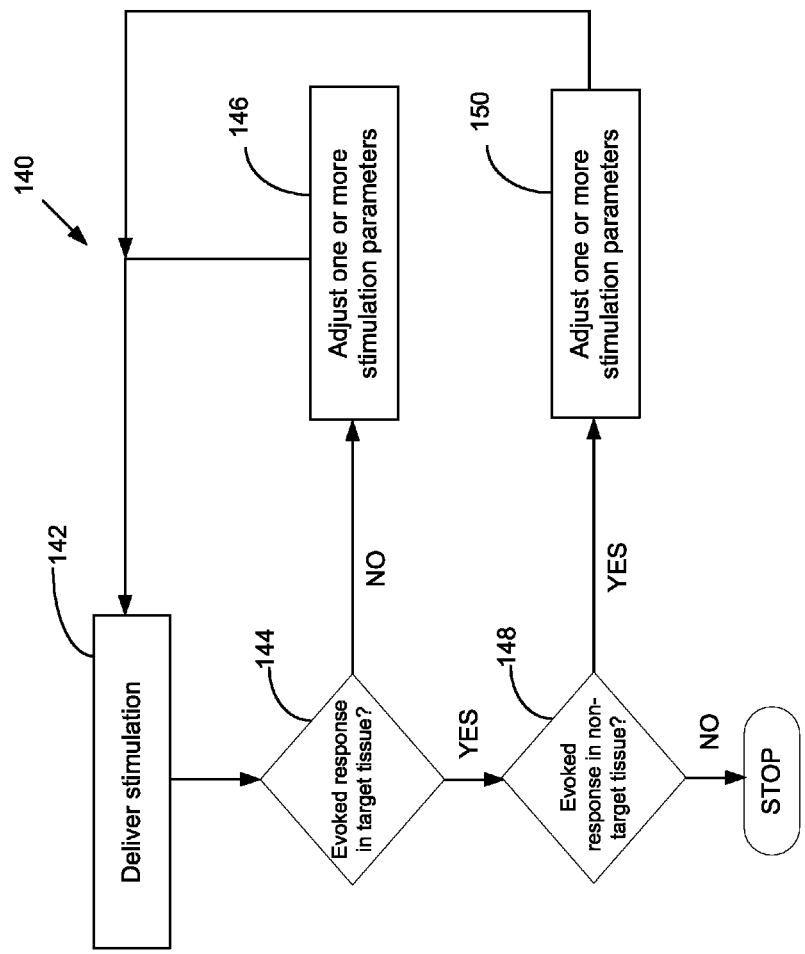
FIG. 9 is a flow chart illustrating an embodiment of adjusting one or more stimulation parameters to excite target tissue while reducing excitation of non-targeted tissue.

FIG. 9 shows a method 140 for a calibration process in which stimulation parameters are determined to provide a first, desired evoked response in target tissue while not producing a second, undesired response in other tissue ("untargeted" tissue). For example, it may be desired to induce action potentials on the patient's vagus nerve, but not to stimulate other tissue such as the patient's vocal cords. Thus, electrodes may be placed on or adjacent the targeted tissue (e.g., the vagus nerve) and the untargeted tissue (e.g., the vocal cords) and the method 140 of FIG. 9 can be performed to permit the IMD 10 to be configured to adjust the stimulation to produce the first, desired response in the targeted tissue, but not produce the second, undesired response in the untargeted tissue. Method 140 may be performed during implantation of the IMD 10 in the patient or after implantation during a calibration mode of operation as effectuated by, for example, the programming system 20.

Referring again to FIG. 9, a stimulation is delivered to the targeted tissue at 142. After the stimulation is delivered, a decision is made at 144 to determine whether the targeted tissue has been excited (i.e., whether the first, desired evoked response has occurred). This determination can be made in accordance with any of a variety of techniques, such as those described above involving sensing of the targeted tissue such as a cranial nerve. If the targeted tissue has not been excited, then at 146 the method comprises adjusting one or more stimulation parameters (e.g., current magnitude, frequency, duration, etc.) and looping back to block 142 and repeating blocks 142, 144, and 146 until the targeted tissue is excited by the delivered stimulation.

Once the IMD 10 has been configured to excite the targeted tissue, the method continues at decision 148 to determine whether the untargeted tissue has been excited. If the untargeted tissue is not excited, then the method 140 stops. If, however, the untargeted tissue is excited by the delivered stimulation at 142, the method comprises at 150 adjusting one or more stimulation parameters (e.g., current magnitude, frequency, duration, etc.) and looping back to block 142 to repeat the process until the stimulation parameters are set so that targeted is excited, but untargeted tissue is not excited. The parameters set as a result of the method of FIG. 9 are used to operate the IMD to provide future neurostimulation therapy.

Determining whether the untargeted tissue is excited may comprise the same or similar techniques implemented to determine whether the targeted tissue is excited, such as determining whether a sensed voltage threshold is exceeded in for the untargeted tissue, or by the patient or a healthcare provider manually signaling to the device (using, e.g., a magnet) whether or not the untargeted tissue has been excited. In some embodiments, the method of FIG. 9 achieves a configuration for the IMD that causes the IMD to excite targeted tissue, but not excite untargeted tissue. In other embodiments, the configuration causes the IMD to excite targeted tissue, but reduce the excitation of untargeted tissue.

Figure 10:
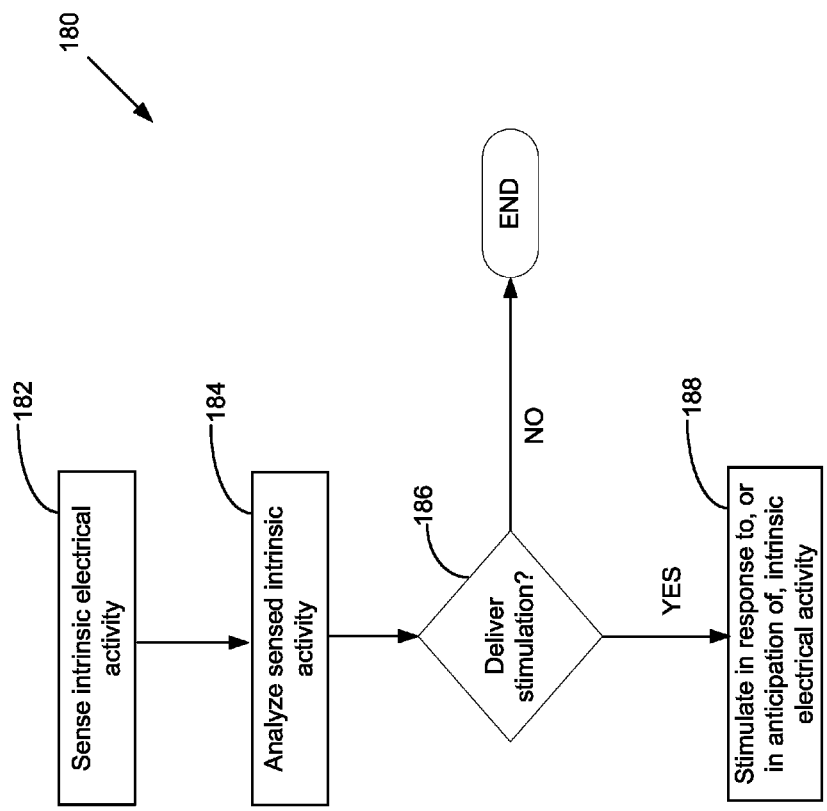
FIG. 10 is a flow chart illustrating an embodiment of stimulating in response to intrinsic electrical activity.

FIG. 10 shows a method embodiment 180 in which the IMD 10 stimulates a nerve (e.g., a cranial nerve such as the vagus nerve) based on the intrinsic electrical activity of the nerve. The intrinsic electrical activity of the nerve comprises the activity of the nerve other than electrical activity induced by an artificial stimulus such as that provided by the IMD 10, i.e., it is the electrical activity native to the patient. Stimulating based on sensed intrinsic electrical activity of the nerve can be used to block such intrinsic signals. Stimulating based on the intrinsic electrical activity of the nerve may be used to enhance the therapeutic benefit of neurostimulation therapy. For example, at least some afferent intrinsic signals from various parts of the body may interfere with vagus nerve stimulation. Blocking such intrinsic signals may increase the efficacy of vagus nerve stimulation provided by the IMD 10, which may induce "extrinsic" action potentials on the nerve. "Blocking" such intrinsic signals may comprise reducing the amplitude of, or completely eliminating the signals. Alternatively, a vagus nerve stimulator may be more effective when its stimulation is delivered during periods of low or high intrinsic activity on the vagus nerve. The IMD 10 of the preferred embodiment can be configured to sense a patient's intrinsic nerve signals and (a) to provide stimulation to block afferent or efferent intrinsic nerve signals, (b) to provide stimulation during periods of low intrinsic activity, and/or (c) to provide stimulation during periods of high intrinsic activity. The programming system 20, for example, can be used to dictate the desired response-(a), (b), or (c).

Referring again to FIG. 10, at 182, the method comprises sensing the intrinsic electrical activity of the nerve. The method further comprises analyzing the sensed intrinsic activity, as depicted at 184 of FIG. 10. Analysis of the sensed intrinsic activity may comprise storing the intrinsic signals over a first time interval and analyzing those signals by a software algorithm to determine whether stimulation from the IMD 10 should be applied to the nerve. Following the analysis of the intrinsic activity, a decision is made at 186 as to whether or not the IMD 10 should deliver stimulation to the nerve. If no stimulation is desired, the method ends. If stimulation is desired, the method comprises stimulating in response to, or in anticipation of, the intrinsic electrical activity of the nerve, as illustrated as 188 of FIG. 10. The stimulation produced at 184 may be used to block the intrinsic activity on the nerve from reaching the brain or to increase the efficacy of vagus nerve stimulation as noted above.

In accordance with at least some embodiments of the invention, the IMD 10 may comprise any or more or all of: a stimulation delivery module, a signal capture module, an adjustment module, and an increment module. In some embodiments, the stimulation module may deliver an electrical signal from a pulse generator (discussed above) to a nerve. The signal capture module may determine whether a first evoked neural response has occurred on the nerve as a result of the stimulation. The adjustment module may adjust one or more of the plurality of stimulation parameters if the first evoked response has not occurred. The increment module may cause the stimulation delivery, signal capture and increment modules to repeat their operations until the first evoked neural response occurs. These, or other modules, may perform any of the functions described herein. The various modules are implemented in software, firmware, hardware, or any suitable combination thereof.

While the preferred embodiments of the present invention have been shown and described, modifications thereof can be made by persons skilled in the art without departing from the spirit and teachings of the invention. The embodiments described herein are exemplary only, and are not intended to limit the scope of protection provided herein.

What is claimed is:

1. An implantable medical device, comprising:
a pulse generator that provides an electrical pulse signal to stimulate a cranial nerve in a patient, wherein said electrical pulse signal comprises multiple stimulation parameters;
a stimulation lead assembly coupled to said pulse generator for delivering said electrical pulse signal to said cranial nerve, said lead assembly having a proximal end coupled to said pulse generator and a distal end comprising a stimulation electrode assembly adapted to be coupled to said cranial nerve;
a first sensor coupled to said pulse generator, wherein said first sensor is adapted to sense an evoked response in a target tissue;
a second sensor coupled to said pulse generator, wherein said second sensor is adapted to sense an evoked response in a non-target tissue; and
wherein said pulse generator adjusts at least one stimulation parameter to evoke a response in said target tissue and to not evoke a response in said non-target tissue.

2. The implantable medical device of claim 1 wherein said cranial nerve comprises a vagus nerve.

3. The implantable medical device of claim 1 wherein said plurality of stimulation parameters comprise:
current magnitude;
pulse frequency;
pulse width;
an on-time; and
an off-time.

4. The implantable medical device of claim 1 wherein said target tissue comprises said patient's cranial nerve.

5. The implantable medical device of claim 1 wherein the target tissue comprises a specific nerve fiber type of said cranial nerve.

6. The implantable medical device of claim 5 wherein the specific nerve fiber type is selected from the group comprising:
- A fibers;
- B fibers; and
- C fibers.

7. The implantable medical device of claim 1 wherein the non-target tissue comprises said patient's vocal cords.

8. The implantable medical device of claim 1 wherein the non-target tissue comprises said patient's heart.

9. The implantable medical device of claim 1 wherein the non-target tissue comprises a specific nerve fiber type of said cranial nerve.

10. The implantable medical device of claim 9 wherein the specific nerve fiber type is selected from the group comprising:
- A fibers;
- B fibers; and
- C fibers.

11. The implantable medical device of claim 8 utilized to treat heart failure.

12. An implantable medical device to treat heart failure, comprising:
- a pulse generator that provides an electrical pulse signal to stimulate a cranial nerve in a patient, wherein said electrical pulse signal comprises multiple stimulation parameters;
- a stimulation lead assembly operatively coupled to said pulse generator;
- a first sensor communicatively coupled to said pulse generator, wherein said first sensor is adapted to sense an evoked response in a target tissue;
- a second sensor communicatively coupled to said pulse generator, wherein said second sensor is adapted to sense an evoked response in a non-target tissue; and
- wherein said pulse generator adjusts at least one stimulation parameter to evoke a response in said target tissue and to not evoke a response in said non-target tissue.

13. The implantable medical device of claim 12 wherein said cranial nerve comprises a vagus nerve.

14. The implantable medical device of claim 12 wherein said target tissue comprises said patient's cranial nerve.

15. The implantable medical device of claim 12 wherein said target tissue comprises a specific nerve fiber type of said cranial nerve.

16. The implantable medical device of claim 15 wherein the specific nerve fiber type is selected from the group comprising:
- A fibers;
- B fibers; and
- C fibers.

17. The implantable medical device of claim 12 wherein the non-target tissue comprises said patient's vocal cords.

18. The implantable medical device of claim 12 wherein the non-target tissue comprises said patient's heart.

19. The implantable medical device of claim 1 wherein said non-target tissue comprises a specific nerve fiber type of said cranial nerve.

20. An implantable medical device to treat heart failure, comprising:
- a pulse generator that provides an electrical pulse signal to stimulate a branch of a vagus nerve in a patient, wherein said electrical pulse signal comprises multiple stimulation parameters;
- a stimulation lead assembly coupled to said pulse generator for delivering said electrical pulse signal to said vagus nerve, said lead assembly having a proximal end coupled to said pulse generator and a distal end comprising a stimulation electrode assembly adapted to be coupled to said vagus nerve;
- a first sensor coupled to said pulse generator, wherein said first sensor is adapted to sense an evoked response in said vagus nerve;
- a second sensor communicatively coupled to said pulse generator, wherein said second sensor is adapted to sense an evoked response in said patient's vocal cords; and
- wherein said pulse generator adjusts at least one stimulation parameter to evoke a response in said vagus nerve and to not evoke a response in said patient's vocal cords.

* * * * *